US 8,043,218 B2

(12) United States Patent
Chapelon et al.

(10) Patent No.: US 8,043,218 B2
(45) Date of Patent: Oct. 25, 2011

(54) THERAPEUTIC ENDOCAVITY PROBE COMPRISING AN IMAGE TRANSDUCER INTEGRATED WITHIN THE THERAPY ULTRASONIC TRANSDUCER

(75) Inventors: Jean-Yves Chapelon, Villeurbanne (FR); Laura Curiel, Toronto (CA); Yves Martin, Beynost (FR); Olivier Nallet, Lyons (FR)

(73) Assignees: EDAP S.A., Vaulx-en-Velin (FR); Institut National de la Sante et de la Recherche Medicale I.N.S.E.R.M., Paris Cedex (FR)

( * ) Notice: Subject to any disclaimer, the term of this patent is extended or adjusted under 35 U.S.C. 154(b) by 980 days.

(21) Appl. No.: 11/817,277

(22) PCT Filed: Mar. 15, 2006

(86) PCT No.: PCT/FR2006/050229
§ 371 (c)(1),
(2), (4) Date: Dec. 17, 2007

(87) PCT Pub. No.: WO2006/097661
PCT Pub. Date: Sep. 21, 2006

(65) Prior Publication Data
US 2008/0214964 A1 Sep. 4, 2008

(30) Foreign Application Priority Data
Mar. 15, 2005 (FR) ...................................... 05 02531

(51) Int. Cl.
*A61B 8/00* (2006.01)
*A61B 8/14* (2006.01)
(52) U.S. Cl. .......................... 600/439; 600/459; 600/462

(58) Field of Classification Search .................. 600/439, 600/459
See application file for complete search history.

(56) References Cited

U.S. PATENT DOCUMENTS

| 5,474,071 | A | * | 12/1995 | Chapelon et al. | ............. 600/439 |
| 5,666,954 | A | * | 9/1997 | Chapelon et al. | ............. 600/439 |
| 5,720,286 | A | | 2/1998 | Chapelon et al. | |
| 5,720,287 | A | * | 2/1998 | Chapelon et al. | ............. 600/439 |
| 5,873,828 | A | | 2/1999 | Fujio et al. | |
| 6,071,238 | A | * | 6/2000 | Chapelon et al. | ............. 600/439 |
| 6,371,903 | B1 | * | 4/2002 | Blanc et al. | ......................... 600/2 |
| 6,676,601 | B1 | | 1/2004 | Lacoste et al. | |
| 6,716,184 | B2 | * | 4/2004 | Vaezy et al. | ....................... 601/3 |

FOREIGN PATENT DOCUMENTS
EP 659387 A 6/1995
EP 1034745 A 9/2000
* cited by examiner

*Primary Examiner* — Long V. Le
*Assistant Examiner* — Angela M Hoffa
(74) *Attorney, Agent, or Firm* — Dennison, Schultz & MacDonald

(57) ABSTRACT

A therapeutic endocavity probe for treating tissues in particular of the prostate by emission of focused ultrasonic waves, including a support forming a guide tube extended by a mounting head for at least one therapy transducer component with an active surface emitting focused ultrasonic waves and having a spherical front of a total surface area in which a surface window is laid out for mounting an imaging transducer. According to the invention, the therapy transducer component has a front face having a total surface area equal to the sum of the active surface area equal to 1,500 mm²±200 mm², and of the surface area of the window for letting through the imaging transducer, the ratio of the surface area of the window over the active surface area of the therapy transducer component being less than or equal to 0.45.

20 Claims, 4 Drawing Sheets

THERAPEUTIC ENDOCAVITY PROBE COMPRISING AN IMAGE TRANSDUCER INTEGRATED WITHIN THE THERAPY ULTRASONIC TRANSDUCER

BACKGROUND OF THE INVENTION

The present invention relates to a therapy endocavity probe with which tissues in particular of the prostate may be treated by pulsed and focused ultrasonic acoustic waves on the one hand, and these tissues may be viewed on the other hand.

In the state of the art, the use of an imaging transducer in association with a therapy transducer emitting focused ultrasonic waves is known, providing real-time follow-up of the tissues.

In the field of extracorporeal applications, there are various embodiments of probes with imaging. For example, Lizzi et al. in *"Ultrasonic hyperthermia for ophthalmic therapy' IEEE Trans. Ultrason., Ferroelec., Freq., Contr.*, 31, pp. 473-481" describe an echographic probe for an ophthalmologic application whereas Vallencien et al. (1996) in *"'Ablation of superficial bladder tumors with focused extracorporeal pyrotherapy' Urology*, 47, pp. 204-207" and Wu et al. in *"'Pathological changes in human malignant carcinoma treated with high-intensity focused ultrasound', Ultrasound in Med & Biol.*, 27, pp. 1099-1106" propose extracorporeal probes with large sizes where the surface area occupied by the imaging transducer is negligible relatively to the surface area generating the ultrasonic waves.

If for extracorporeal applications, tissue imaging does not pose any particular problem, this is not the case for an endocavity probe such as an endorectal probe, considering problems notably related to the reduced bulk which such a probe should have. In order to attempt to solve this problem, Vaezy et al. in *"Real-time visualization of high-intensity focused ultrasound treatment using ultrasound imaging", Ultrasound in Med. & Biol.*, vol. 27(1), pp. 33-42, 2001" propose a probe including an imaging transducer located at the end of a therapy transducer. The main drawback of this probe lies in the fact that the axis of the image is not oriented along the focusing axis of the therapy transducer. Further, the relative positioning of both of these transducers does not facilitate its use under endocavity conditions.

Sanghvi et al. in their U.S. Pat. No. 5,117,832 propose an endocavity probe including a therapy transducer at the centre of which an imaging transducer is placed. To remedy the problem of the surface area loss of the therapy transducer, the imaging transducer is also used for therapy. Both transducers therefore have the same operating frequency or close operating frequencies which result from a compromise between the therapy frequency and the imaging one. The result is an altered image quality and/or treatment performances which are not optimum.

Also, the endorectal probe presented at the ISTU 2002 Congress by Ishida K, Kubota J, Mitake T, Carlson R F, Seip R, Sanghvi N T, Asuma T, Sasaki K, Kawabata K, Umemura S, in *"Development and animal experiment of variable focusing HIFU system for prostate cancer treatment"* includes an imaging probe with a rectangular shape, housed in the centre of the therapy probe. Even if such a probe is designed for endorectal application, its very large size precludes such an application in practice.

Analysis of known prior solutions leads to the observation that there appears the need for having a probe with dimensions allowing endocavity use, while being provided with a transducer capable of performing good quality imaging in real time, combined with a therapy transducer, with treatment performances which are not affected by the presence of the imaging transducer In order to meet such a need, the applicants are worthy in that they sought a solution in the direct integration of the imaging transducer within the therapy transducer even if such a solution first leads to degradation of the therapeutic performance. Moreover, it was observed that this degradation of performance is accompanied by dispersion of acoustic energy, capable of generating undesirable secondary lesions. Surprisingly, a specific geometry between the imaging and therapeutic transducers, with which a probe may be made, which allows endocavity use, while providing real time follow-up and therapeutic effectiveness, was found in particular.

SUMMARY OF THE INVENTION

The object of the invention therefore aims at proposing a therapeutic endocavity probe for treating tissues by emission of focused ultrasonic waves, including a support having a longitudinal axis and forming a guide tube extended by a mounting head for at least one therapy transducer component with an active surface emitting focused ultrasonic waves and having a spherical front face with a total surface area in which a window with a determined surface is provided for mounting an imaging transducer, the transducer component having a first diameter in the direction perpendicular to the longitudinal axis, which is smaller than a second diameter considered along the longitudinal axis. According to the invention, the therapy transducer component has a front face having a total surface area equal to $1500 \text{ mm}^2 \pm 200 \text{ mm}^2$, increased by the surface area of the window for letting through the imaging transducer, the ratio of the window surface area over the active surface area of the therapy transducer component being less than or equal to 0.45.

According to a preferred exemplary embodiment the ratio between the window surface area over the active surface area of the therapy transducer component is between 0.45 and 0.25.

For example, the first diameter of the therapy transducer component is between 33 and 40 mm.

According to another aspect of the invention, the therapy transducer component has a geometrical focal length between 35 and 45 mm.

According to another aspect of the invention, the therapy transducer component emits ultrasonic waves with a pulse duration located in the range from 4 to 7 s and advantageously equal to 6 s, the ultrasonic waves being separated by at extinction duration located in the range from 4 to 7 s and advantageously equal to 4 s.

According to another aspect of the invention, the therapy transducer component provides peak ultrasonic intensity at the focal point, between 500 and $3,000 \text{ W/cm}^2$ and preferably between 1,000 and $1,500 \text{ W/cm}^2$.

Preferably, the therapy transducer component has an operating frequency between 2 and 5 MHz and preferably equal to 3 MHz.

According to an advantageous embodiment feature, the imaging transducer is mounted on the head independently of the therapy transducer component.

According to this preferred exemplary embodiment, the imaging transducer is removably mounted on the head which has an open front portion to allow positioning of the therapy transducer component, and a rear portion provided with a flap in order to allow access to the imaging transducer.

In an exemplary embodiment, the imaging transducer is removably mounted on a supporting olive on the head, extending and protruding from the front face of the therapy transducer component.

In an exemplary embodiment, the imaging transducer is mounted so that the image plane formed by said imaging transducer is transverse or longitudinal relatively to the longitudinal axis of the probe.

According to an alternative embodiment, it should be noted that displacement means act on the supporting olive so as to provide its rotation so that the imaging transducer may alternately form a transverse and then a longitudinal imaging plane.

It seems to be particularly advantageous if the imaging transducer and the therapy transducer component are mounted so that the focusing axis of the therapy transducer component is comprised in the imaging plane of the imaging transducer.

Preferably, the imaging transducer has a central frequency between 5 and 10 MHz and preferably equal to 7.5 MHz.

According to a preferred embodiment, the head surrounds the therapy transducer component via a distal edge with a circular profile extending opposite to a proximal edge which is part of a frusto-conical section for connecting to the guide tube. The distal edge extending on either side via chamfers for connecting to longitudinal edges with circular profiles connected to the frusto-conical section.

According to this preferred alternative embodiment, the frusto-conical connection section includes a channel for feeding a coupling liquid and a channel for recovering the coupling liquid, connected to feed conduits and recovery conduits respectively, placed inside the guide tube, each channel opening out from the proximal edge at each longitudinal edge.

Preferably, the guide tube has a circular transverse cross-section and in proximity to the frusto-conical connection section, positioning and sealing grooves for a membrane able to confine the head of the probe.

The supporting olive of the imaging transducer in order to allow it to be introduced into an endocavity extends back from the plane tangent to the proximal edge and to the distal edge.

Advantageously, the head is laid out so that the plane tangent to the proximal edge and to the distal edge is convergent towards the distal edge.

Another aspect of the invention is to propose an apparatus for treating tissues including a therapy endocavity probe according to the invention.

Another aspect of the invention is to propose a treatment apparatus including a probe of the endocavity type for treating tissues of the prostate.

According to another application, the object of the invention aims at proposing a treatment apparatus including a probe of the endovaginal or coelioscopic type.

BRIEF DESCRIPTION OF THE DRAWINGS

Various other features will become apparent from the description made below with reference to the appended drawings which show embodiments of the object of the invention, as non-limiting examples.

DESCRIPTION OF THE PREFERRED EMBODIMENTS

Figure 1:
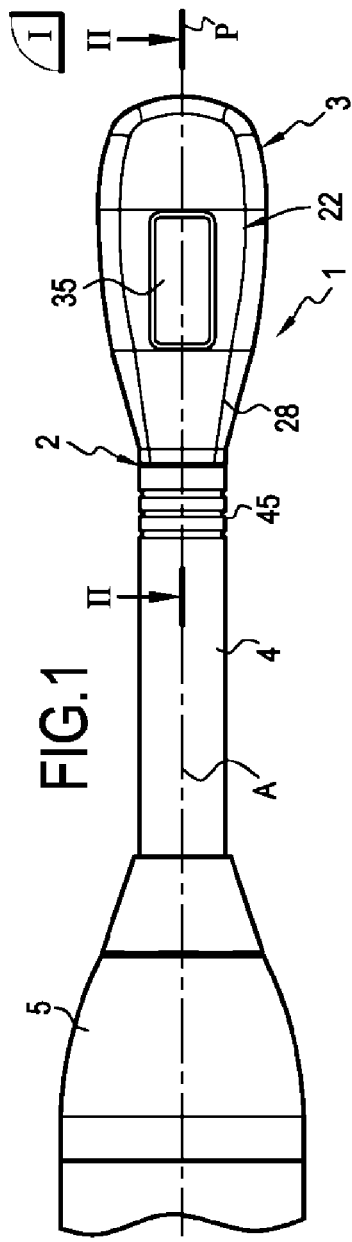
FIG. 1 is a view of a therapeutic endocavity probe in the introduction or treatment position.
Figure 2:
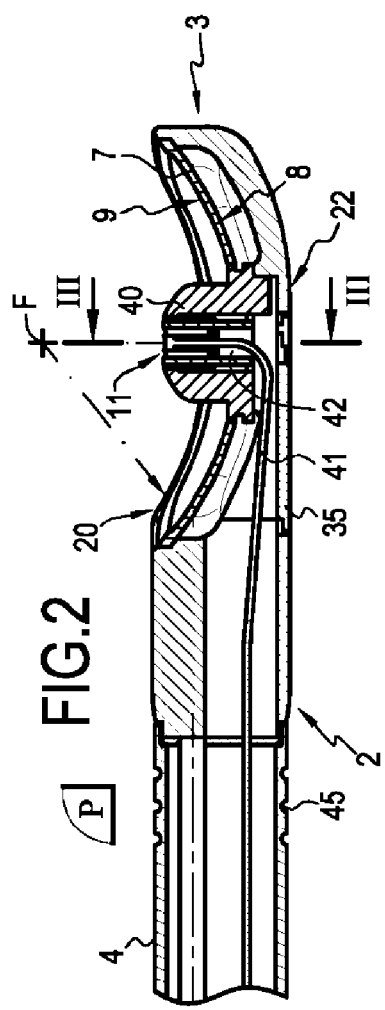
FIG. 2 is a longitudinal sectional view substantially taken along lines II-II of FIG. 1.
Figure 3:
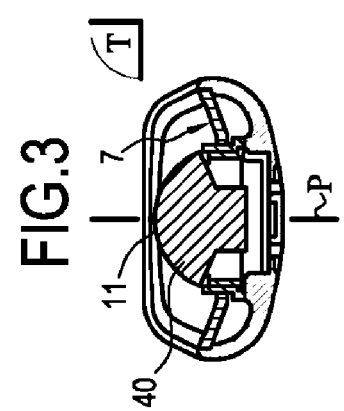
FIG. 3 is a transverse sectional view of the endocavity probe according to the invention substantially taken along lines III-III of FIG. 2.
Figure 5:
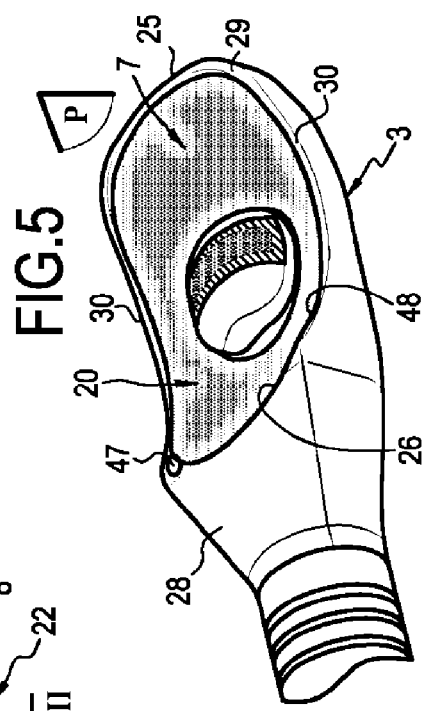
FIG. 5 is a partial perspective view of the endocavity probe according to the invention.

The object of the invention relates to a therapeutic endocavity probe 1 which in a known way is part of an apparatus, not shown, for treating tissues. In the exemplary embodiment illustrated in the figures, the object of the invention is an endocavity probe suitable for destroying tissues in particular of the prostate. Of course, the object of the invention may be applied to other types of probes in order to for example form an endovaginal probe for e.g. treating fibromes, or a coelioscopic probe.

In the illustrated example, the endocavity probe 1 includes a support 2 having a longitudinal axis A and conformed so as to traditionally have a head 3 extended by a guide tube 4 connected to a main body 5 integrating the different means related to the operation of the endocavity probe.

As this is more specifically apparent from FIGS. 2-5, the endocavity prove 1 includes at least one therapy transducer component 7 emitting focused ultrasonic waves. Traditionally, the transducer component 7 is preferably selected from the group of a conventional piezoelectric ceramic or of a mono-component or multi-component composite piezoelectric ceramic. The therapy transducer component 7 has opposite a rear face 8, a spherical front face 9 having a first diameter $d_1$ considered in a transverse plane T perpendicular to the longitudinal axis A, which is smaller than a second diameter $d_2$ considered along the longitudinal axis A. The spherical front face 9 thus covers a total surface area S obtained from consideration of the diameters $d_1$, $d_2$.

The endocavity probe 1 also includes an imaging transducer 11 directly integrated inside the therapy transducer component 7. For this purpose, the spherical front face 9 of the therapy transducer component 7 is laid out so as to include an aperture or a window 12 with a surface $S_2$ suitable for mounting the imaging transducer 11. It should therefore be understood that the spherical front face 9 has a total surface area S which is equal to the sum of the surface area $S_2$ of the window 12 and of an active surface area $S_1$ corresponding to the active portion of the transducer generating the ultrasonic waves.

Figure 4:
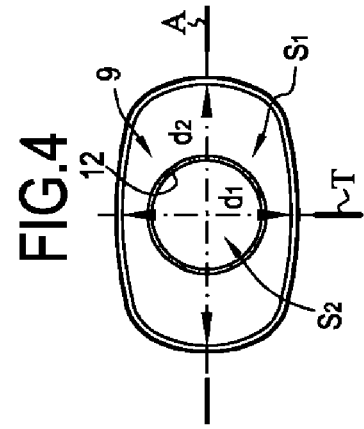
FIG. 4 is a front view of the therapy transducer component according to the invention.

In the illustrated exemplary embodiment, more particularly in FIG. 4, the window 12 laid out in the therapy transducer component 7 has a circular section. Advantageously, the window 12 is laid out so as to be completely integrated inside the spherical front face, i.e., so as to be completely surrounded by said transducer component 7. The window 12 is thus placed in the middle or at the centre of the therapy transducer component 7. According to a preferred alternative embodiment, the window 12 is centered relatively to the therapy transducer component 7 so that the focusing axis F of the therapy transducer component is comprised in the imaging plane of the imaging transducer 11. Of course, it may be considered that a shift exists between the imaging plane and the focal axis of the therapy transducer component 7.

According to the invention, the therapy transducer component 7 has an active surface area $S_1$ equal to 1,500 mm$^2$±200 mm$^2$. In other words, the spherical front face 9 has a total surface area S equal to $1,500 \text{ mm}^2 \pm 200 \text{ mm}^2$, increased by the surface area $S_2$ of the window 12.

According to another feature of the object of the invention, the ratio of the surface area $S_2$ of the window 12 over the active surface area $S_1$ of the therapy transducer component 7 is less than or equal to 0.45. Preferably, the ratio of the surface area $S_2$ of the window 12 over the active surface area $S_1$ is between 0.45 and 0.25.

According to another feature of the invention, the first diameter $d_1$ of the therapy transducer component 7 is between 33 and 40 mm so as to allow for intra-corporeal introduction.

According to another feature of the invention, the therapy transducer component 7 has a geometrical focal length corresponding to the radius of the spherical front face 9, between 35 and 45 mm.

The therapy transducer component 7 is mounted in the head of the support 3 in order to be protected while providing emission of ultrasonic waves. The supporting head 3 forms a closed component having a front face 20 in which an aperture is laid out into which the spherical front face 9 of the therapy transducer component 7 may extend, thereby allowing ultrasonic waves to be emitted. It may be considered that the front face 20 of the supporting head 3 thereby opens out in an introduction plane I perpendicular to the transverse plane T and to the focusing plane P passing through the longitudinal axis A and the focusing axis F of the therapy transducer component 7.

The head 3 has, opposite to the front face 20, a rear face 22 extended by edges which will surround very closely the therapy transducer component 7 according to a complementary shape of the contour of said component 7. In this respect, the head 3 thus has in the introduction plane I, a distal edge 25 with a circular profile extending opposite to a proximal edge 26 being part of a frusto-conical connecting section 28 of the guide tube 4. The distal edge 25 extends on either side, with chamfers 29 connecting to longitudinal edges 30 with a circular profile connected to the frusto-conical section 28.

According to another feature of the invention, the imaging transducer 11 is mounted on the head 3 independently of the therapy transducer component 7. Preferably, the imaging transducer 11 is removably mounted relatively to the head 3 so as to allow its replacement. For this purpose, the rear face 22 of the head 3 is provided with flap 35, the withdrawal of which provides access to the imaging transducer 11.

In the illustrated exemplary embodiment, the imaging transducer 11 is formed with a curved network of transducer components advantageously removably mounted on a supporting member such as an olive 40 attached on the head 3 for example by adhesive bonding. In the illustrated example, the image plane formed by the imaging transducer 11 is transverse, i.e., it is perpendicular to the longitudinal axis A of the probe. Such a network of transducer components is powered by a cable 41 placed inside one channel 42 provided in the olive and communicating with the inside of the head and of the guide tube 4 so as to allow said cable 41 to be mounted.

According to another embodiment, it should be noted that the olive 40 may be attached in a position perpendicular to the one described earlier so that the image plane formed by the imaging transducer is oriented along the longitudinal axis A of the probe.

According to another embodiment, displacement means of any types act on the olive 40 so as to provide its rotation in order to allow the imaging transducer 11 to alternately form a transverse and then a longitudinal image plane.

In the illustrated example, the supporting olive 40 extends and protrudes from the front face 9 of the therapy transducer component 7. However the supporting olive 40 of the imaging transducer 11 extends back from the plane tangent to the proximal edge 26 and to the distal edge 25. Preferably, it should be noted that the head 3 is laid out so that the plane tangent to the proximal edge 26 and to the distal edge 25 is convergent towards the distal edge.

Of course, an embodiment may be contemplated, in which the imaging transducer 11 substantially extends at the level of the spherical front face 9, or even set back relatively to the latter.

According to another feature of the invention, the therapy transducer component 7 emits ultrasonic waves with a pulsed duration located in the range from to 1 to 20 s and preferably between 4 and 7 s and advantageously equal to 6 s. Complementarily, the ultrasonic waves are separated from each other by an extinction duration between 1 and 20 s and preferably between 4 and 7 s, and advantageously equal to 6 s. Advantageously, the therapy transducer component provides peak ultrasonic intensity at the focal point (I Spatial Peak Temporal Peak) between 500 and 3,000 $\text{W/cm}^2$ and preferably between 1,000 and 1,500 $\text{W/cm}^2$.

It should be noted that the therapy transducer component 7 has an operating frequency between 2 and 5 MHz and preferably equal to 3 MHz whereas the imaging transducer 11 has a central frequency between 5 and 10 MHz and preferably equal to 7.5 MHz.

According to another feature of the invention, the head 3 of the probe is intended to be confined in a membrane, not shown, but known per se. For this purpose, the guide tube 4 has a circular transverse cross-section and has, in proximity to the frusto-conical connecting section 28, grooves 45 providing the mounting and positioning of such a membrane but also the seal.

According to a preferred exemplary embodiment, the frusto-conical connecting section 28 includes a channel 47 for feeding a coupling liquid and a channel 48 for recovering the coupling liquid, connected to feed and recovery conduits, respectively, placed inside the guide tube 4. Each channel 47, 48 opens out from the proximal edge 26 at each longitudinal edge 30 of the support.

As apparent from the foregoing description, with the endocavity probe 1 according to the invention, it is possible to obtain a therapeutic performance equivalent to that of a therapy transducer with an emission surface $S_1$ without any imaging transducer. Such an equivalence is obtained by suitably selecting the relative geometry between the therapy 7 and imaging 11 transducers, preferably combined with a selection of operating parameters of the therapy transducer 7. Thus, by means of a probe equipped with a therapy transducer component 7 having the features according to the invention and emitting ultrasonic waves with a pulsed duration equal to 6 s, and an extinction duration equal to 4 s, it is possible to obtain, within the scope of destroying tumoral tissues of the prostate, lesions equivalent to those obtained with a probe without any imaging transducer.

With the probe according to the invention, is it thereby possible to control dispersion of acoustic energy likely to generate undesirable secondary lesions. Indeed, the presence of the window 12 at the centre of the therapy transducer component 7 leads to the appearance of so-called secondary energy lobes which may for example intervene at the rectum when a deep lesion is made in the prostate. The secondary lobes result from the significant change in the geometry of the therapy transducer component 7, due to the window 12 but also to the loss of active surface area of the therapy transducer component 7.

It appears that the significance of these secondary lobes increases depending on the increase in the surface area $S_2$ of the window 12. Thus, as a result, for a ratio $S_2/S_1 > 0.45$, the ratio of the measured acoustic pressure for example at the rectal wall over the acoustic pressure measured at the focal point substantially increases. Thus for example, for a ratio $S_2/S_1=1$, this ratio is equal to −12 dB whereas for a ratio $S_2/S_1=0.45$, this ratio is equal to −16 dB. Experiment shows that when the ratio of the acoustic pressure measured at the rectal wall over the acoustic pressure measured at the focal point exceeds the threshold of −16 dB, the risk of heating becomes too substantial and may generate irreversible biological lesions. Indeed, in this situation, the pressure differential between the focal point of the therapy transducer and the rectal wall for example is insufficient for confining the biological lesion to the focal area. It is therefore important for the safety of the patient to control the pressure at the rectal wall and in order to do this, to retain a surface ratio $S_2/S_1$ less than 0.45.

Figure 6A:
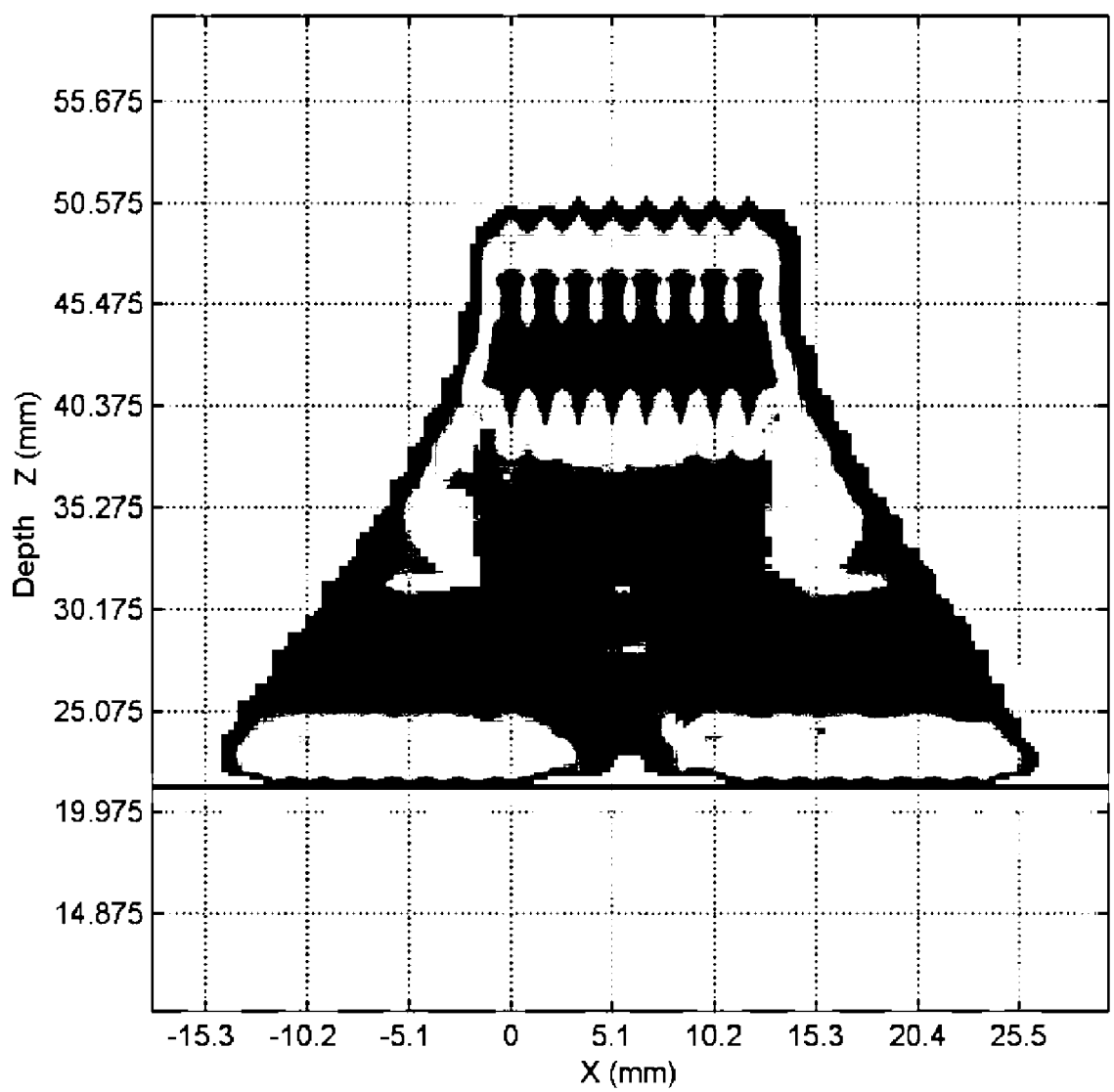
FIGS. 6A-6C represent a calculation of the biological lesions obtained in the tissues for different ratios of the surface area of the imaging window over the active surface area of the therapy transducer component.
Figure 6B:
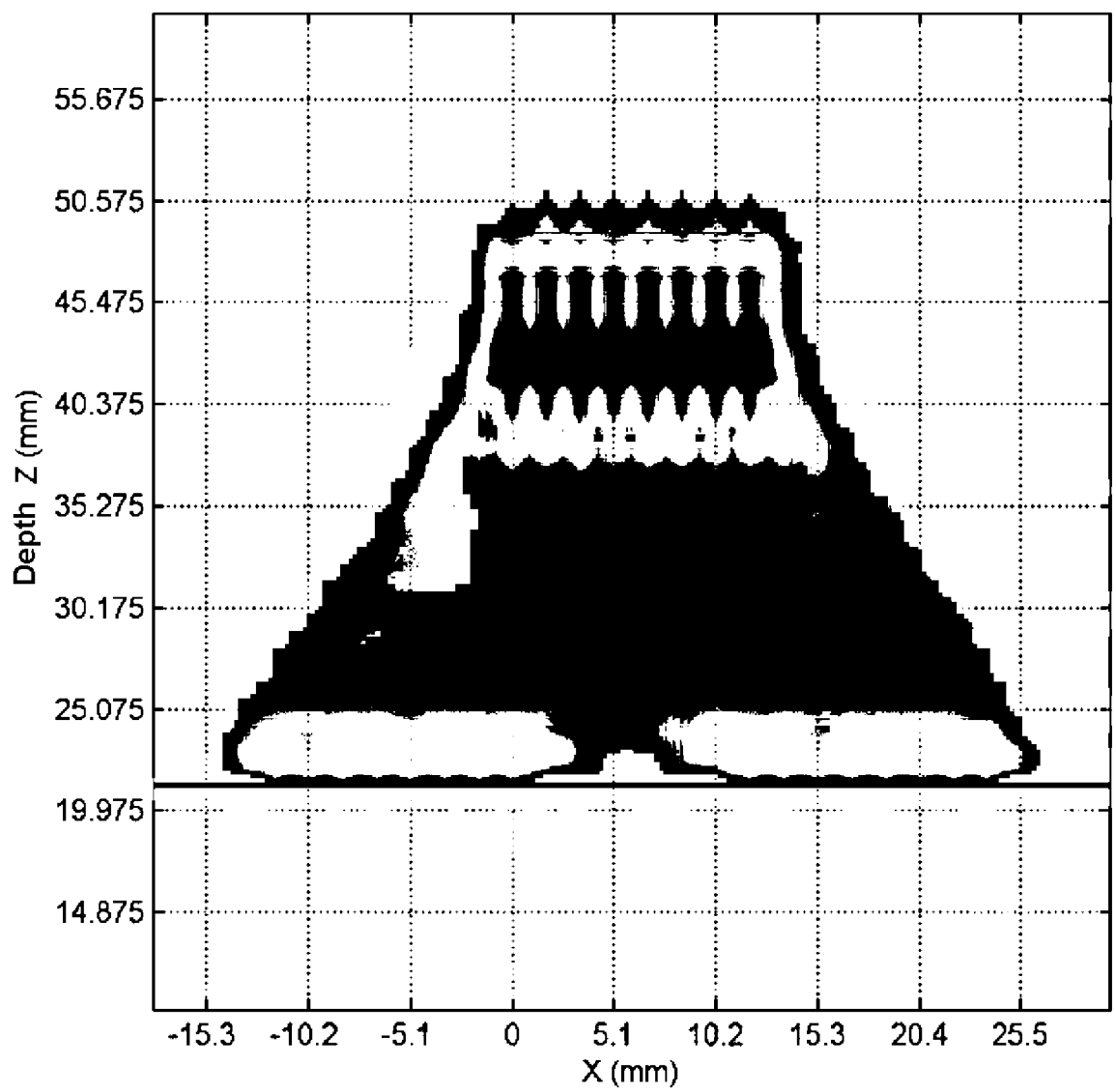
Figure 6C:
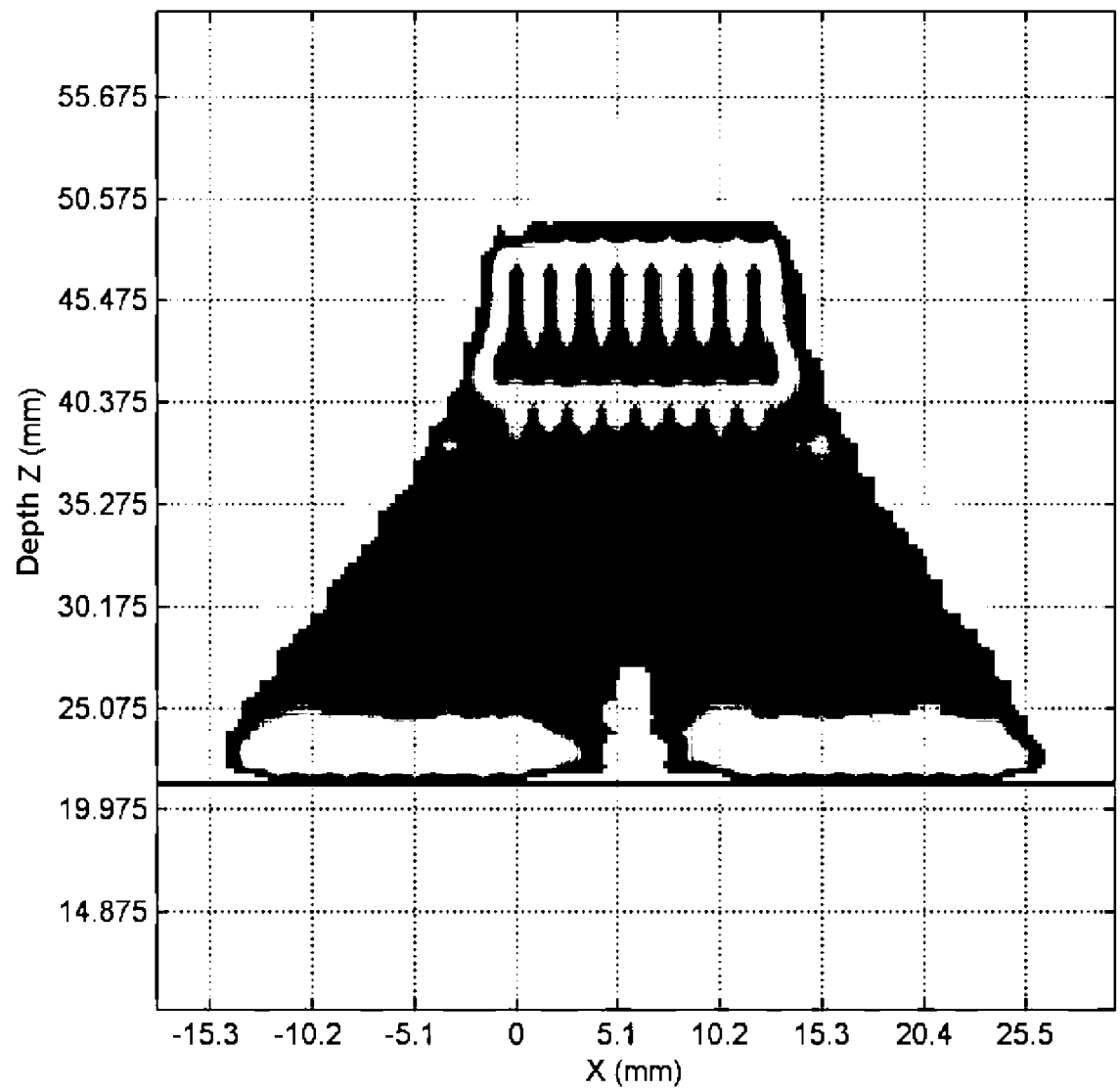

FIGS. 6A-6C respectively illustrate the shape of the biological lesion for $S_2/S_1$ ratios of 0.37, 0.49 and 1.08, respectively.

In FIG. 6A, a homogenous lesion in the treated volume may be observed. In FIGS. 6B and 6C, at the centre and at the base of the treatment volume, an untreated area is formed which assumes the shape of a notch. Also, a strong reduction of the heat dose at the focal point may be observed (appearance of well differentiated elementary lesions) as well as in the core of the targeted area (about a two-fold smaller heat dose). These figures also confirm the increase of the heat dose at the rectal wall and which exceeds the admissible threshold in FIG. 6C.

In order to maintain a satisfactory heat dose and a homogenous treatment space as shown in FIG. 6A, the acoustic power of the transducer then needs to be increased. This increase causes an increase in the pressure and the heat dose at the rectal wall generating a quasi-certain rectal lesion in the case of a ratio $S_2/S_1=1.08$ and possible lesion in the case of ratio $S_2/S_1=0.49$. These figures confirm the requirement of maintaining a ratio $S_2/S_1$ less than or equal to 0.45.

The invention is not limited to the described and illustrated examples as different modifications may be made thereto without departing from the scope thereof.

The invention claimed is:

1. A therapeutic endocavity probe for treating tissues by emitting focused ultrasonic waves, comprising:
a support having a longitudinal axis (A) and forming a guide tube extended by a mounting head;
at least one therapy transducer component received in said mounting head and having an active surface area ($S_1$) emitting focused ultrasonic waves, the therapy transducer component having a concave front face with a total surface area (S), a first diameter ($d_1$) in a direction perpendicular to the longitudinal axis, and a second diameter ($d_2$) along the longitudinal axis, where diameter ($d_1$) is smaller than the second diameter ($d_2$);
a window in the concave front face of surface area ($S_2$); and
an imaging transducer component mounted in the window;
wherein the active surface area ($S_1$) is 1,500 mm²±200 mm², and the total surface area (S) of the front face of the therapy transducer component is equal to the sum of the active surface area ($S_1$) and the surface area ($S_2$) of the window, with a ratio of the surface area ($S_2$) of the window to the active surface area ($S_1$) of the therapy transducer component being between 0.45 and 0.25.

2. The therapeutic endocavity probe according to claim 1, wherein the first diameter ($d_1$) of the therapy transducer component is between 33 and 40 mm.

3. The therapeutic endocavity probe according to claim 1, wherein the therapy transducer component emits ultrasonic waves with a pulsed duration in the range 4 to 7 s, the ultrasonic waves being separated by an extinction duration in the range 4 to 7 s.

4. The therapeutic endocavity probe according to claim 1, wherein the therapy transducer component provides a peak ultrasonic intensity at the focal point between 500 and 3,000 W/cm².

5. The therapeutic endocavity probe according to claim 1, wherein the therapy transducer component has an operating frequency between 2 and 5 MHz.

6. The therapeutic endocavity probe according to claim 1, wherein the imaging transducer component is mounted on the head independently of the therapy transducer component.

7. The therapeutic endocavity probe according to claim 6, wherein the imaging transducer component is removably mounted on the head which has an open front portion in order to allow positioning of the therapy transducer component, and a rear portion provided with a flap in order to allow access to the imaging transducer component.

8. The therapeutic endocavity probe according to claim 7, wherein the imaging transducer component is removably mounted on an olive-shaped support on the head extending and protruding from the front face of the therapy transducer component.

9. The therapeutic endocavity probe according to claim 8, wherein displacement means acts on the olive-shaped support in order to provide rotation so as to allow the imaging transducer component to alternately form a transverse and then longitudinal image plane.

10. The therapeutic endocavity probe according to claim 6, wherein the imaging transducer component is mounted so that an image plane formed by the imaging transducer component is transverse or longitudinal relative to the longitudinal axis (A) of the probe.

11. The therapeutic endocavity probe according to claim 1, wherein the imaging transducer component and the therapy transducer component are mounted, so that the focusing axis of the therapy transducer component is in the imaging plane of the imaging transducer.

12. The therapeutic endocavity probe according to claim 1, wherein the imaging transducer component has a operational frequency between 5 and 10 MHz.

13. The therapeutic endocavity probe according to claim 1, wherein the head surrounds the therapy transducer component via a distal edge with a circular profile extending opposite to a proximal edge being part of a frusto-conical section for connecting to the guide tube, the distal edge extending on either side by chamfers for connecting to longitudinal edges with circular profiles connected to the frusto-conical section.

14. The therapeutic endocavity probe according to claim 13, wherein the guide tube has a circular transverse cross-section and is in proximity to the frusto-conical connecting sections, with grooves for positioning and sealing a membrane confining the head of the probe.

15. The therapeutic endocavity probe according claim 13, wherein the imaging transducer component is removably mounted on an olive-shaped support on the head extending and protruding from the front face of the therapy transducer component, and
wherein the olive-shaped support of the imaging transducer extends back from the plane tangent to the proximal edge and to the distal edge.

16. The therapeutic endocavity probe according to claim 15, wherein the head is laid out so that a plane tangent to the proximal edge and to the distal edge is convergent towards the distal edge.

17. The therapeutic endocavity probe according to claim 13, wherein the frusto-conical connecting section includes a channel for feeding a coupling liquid and a channel for recovering the coupling liquid connected to feeding and recovery conduits, respectively, placed inside the guide tube, each said channel opening out from the proximal edge at each longitudinal edge.

18. An apparatus for treating tissues, comprising a therapeutic endocavity probe, comprising:
  a support having a longitudinal axis (A) and forming a guide tube extended by a mounting head;
  at least one therapy transducer component received in said mounting head and having an active surface area ($S_1$) emitting focused ultrasonic waves, the therapy transducer component having a generally spherical front face with a total surface area (S);
  a window in the spherical front face of surface area ($S_2$);
  an imaging transducer component mounted in the window, the imaging transducer component having a first diameter ($d_1$) in a direction perpendicular to the longitudinal axis, which is smaller than a second diameter ($d_2$) along the longitudinal axis,
  wherein the total surface area (S) of the front face of the therapy transducer component is equal to the sum of the active surface area ($S_1$), which is 1,500 mm$^2$±200 mm$^2$, and the surface area ($S_2$) of the window, with a ratio of the surface area ($S_2$) of the window to the active surface area ($S_1$) of the therapy transducer component being between 0.45 and 0.25.

19. The treatment apparatus according to claim 18, wherein the probe is an endorectal-type probe for treating prostate tissues.

20. The treatment apparatus according to claim 18, wherein the probe is an endovaginal-type or coelioscopic-type probe.

* * * * *